United States Patent [19]

Duffett et al.

[11] Patent Number: Plant 5,441

[45] Date of Patent: Apr. 16, 1985

[54] CHRYSANTHEMUM PLANT NAMED CAMELOT

[75] Inventors: William E. Duffett, Salinas, Calif.; Grace H. Mack, 108 Wahackme Rd., New Canaan, Conn. 06840

[73] Assignee: Grace H. Mack, New Canaan, Conn.

[21] Appl. No.: 514,318

[22] Filed: Jul. 15, 1983

[51] Int. Cl.[3] ..... A01H 5/00

[52] U.S. Cl. ..... Plt./80

[58] Field of Search ..... Plt./80

*Primary Examiner*—Robert E. Bagwill

*Attorney, Agent, or Firm*—Schwartz, Jeffery, Schwaab, Mack, Blumenthal & Koch

[57] ABSTRACT

A chrysanthemum cultivar named Camelot, identified by the combined characteristics of flat capitulum form, decorative capitulum type, lavender floret color, diameter across face of capitulum up to 55 mm., tall plant height, upright branching pattern, average natural season flowering date of September 25, and average flowering response period of seven weeks in photoperiodic controlled short day programs with good adaptability and performance in April - May controlled pot mum flowerings.

3 Drawing Figures

The present invention comprises a new and distinct cultivar of *Chrysanthemum morifolium,* Ramat., named Camelot.

Camelot is a product of a planned breeding program which had the objective of creating cultivars with decorative capitulum type, short height, spreading branching pattern, durable inflorescence, 6 to 7 week flowering response period, and lavender ray floret color under outdoor natural season conditions.

Camelot was originated from a cross made by Grace H. Mack in a controlled breeding program in New Canaan, Conn. in the year 1977. The female parent was Small Wonder, a light lavender decorative, unpatented and no longer commercially available. The male parent was an unnamed lavender decorative seedling identified as 57 840-1.

Camelot was discovered and selected as a flowering plant within the progeny of the stated cross by William E. Duffett on Oct. 6, 1978 in an outdoor field in Salinas, Calif. The first act of asexual reproduction of Camelot was accomplished when vegetative cuttings were taken from the initial selection in February 1979 under procedures formulated and supervised by William E. Duffett. Horticultural examination of selected units initiated June 1979 has demonstrated that the combination of characteristics herein disclosed for Camelot are firmly fixed and are retained through successive generations of asexual reproduction.

Camelot has not been observed under all possible environmental conditions. The phenotype may vary significantly with variations in environment such as temperature, light intensity, and day length. The following observations, measurements, and comparisons describe plants grown in a field in Salinas, Calif.

Rooted cuttings were established in soil in one gallon containers maintained outdoors under the natural temperature and day length prevailing during July through September. Single pinching was practiced with all branches and buds retained.

The following traits have been repeatedly observed and are determined to be basic characteristics of Camelot which in combination distinguish this chrysanthemum as a new and distinct cultivar:

(1) Flat capitulum form.

(2) Decorative capitulum type.

(3) Lavender ray floret color.

(4) Diameter across face of capitulum up to 55 mm.

(5) Tall plant height.

(6) Upright branching pattern.

(7) Average natural season flowering date of September 28.

(8) Average flowering response period of seven weeks in photoperiodic controlled short day programs with good adaptability and performance in April - May pot mum flowerings.

The accompanying photographic drawings show typical inflorescence and foliage characteristics of Camelot.

Sheet 1 is a color photograph of Camelot.

Sheet 2 is a black and white photograph showing three views of the inflorescence of Camelot.

Sheet 3 is a black and white photograph showing the leaves of Camelot at three stages of development (mature, intermediate, immature).

Of the many commercially available cultivars known to the present inventors, the most similar existing cultivar in comparison to Camelot is Grandchild, unpatented and commercially available.

Reference is made to attached Chart A which compares certain characteristics of Camelot with the same characteristics of Grandchild. It will be noted that in comparison to Grandchild, Camelot has a deeper lavender inflorescence color, one week later natural season flowering date and similar diameter across face of capitulum. Camelot and Grandchild have similar type and form, both develop tall, upright plant habits and display similar permanence of form and color.

In the following description, color references are made to The Royal Horticultural Society Colour Chart. The color values were determined between 3:15 and 3:30 P.M. on Oct. 1, 1982 and 3:15 to 3:30 P.M. on May 16, 1983 under 150 foot-candle light intensity at Salinas, Calif.

Botanical classification: *Chrysanthemum morifolium,* Ramat., cv CAMELOT Early flowering pot and garden mum.

INFLORESCENCE

Capitulum:

*Form.*—Flat.

*Type.*—Decorative.

*Permanence.*—Durable up to 3 weeks. Resists shatter.

*Diameter across face.*—Up to 55 mm.

Corolla of ray florets:

*Color (abaxial).*—74C oxidizing to 65B-D.

*Color (adaxial).*—75B oxidizing to 75C, D.

Reproductive organs:

*Androecium.*—Present disc florets; pollen scant.

*Gynoecium.*—Present both ray and disc florets.

Corola of disc florets:

*Color.*—Immature 1C. Mature 14A.

PLANT

General appearance: Tall, strong, upright branching habit.

Foliage:

*Color (abaxial).*—147A.

*Color (adaxial).*—147B.

Shape: Shallow lobes. Minimum serration.

CHART A

COMPARISON OF CAMELOT AND GRANDCHILD

| | RAY | CAPITU- | AVERAGE NATURAL SEASON |
|---|---|---|---|

CHART A-continued

COMPARISON OF CAMELOT AND GRANDCHILD

| CULTIVAR | FLORET COLOR | LUM FORM AND TYPE | FLOWER DATE | PLANT HEIGHT |
|---|---|---|---|---|
| CAMELOT | LAVENDER | FLAT DECORATIVE | SEPTEMBER 28 | TALL |
| GRANDCHILD | LIGHT LAVENDER | FLAT DECORATIVE | SEPTEMBER 20 | TALL |

| CULTIVAR | BRANCHING PATTERN AND SPREAD | DIAMETER ACROSS FACE OF CAPITULUM | PERMANENCE OF FORM & COLOR |
|---|---|---|---|
| CAMELOT | UPRIGHT | UP TO 55 mm. | UP TO 3 WEEKS |
| GRANDCHILD | UPRIGHT | UP TO 65 mm. | UP TO 3 WEEKS |

COMPARISONS MADE OF PLANTS GROWN UNDER NATURAL SEASON OUTDOOR FIELD CONDITIONS IN SALINAS, CALIFORNIA.

We claim:

1. A new and distinct cultivar of *Chrysanthemum morifolium,* Ramat., plant named Camelot, illustrated and described, and identified by the combined characteristics of flat capitulum form, decorative capitulum type, lavender ray floret color, diameter across face of capitulum up to 55 mm., tall plant height, upright branching pattern, average natural season flowering date of September 28, and average flowering response period of seven weeks in photoperiodic controlled short day programs.

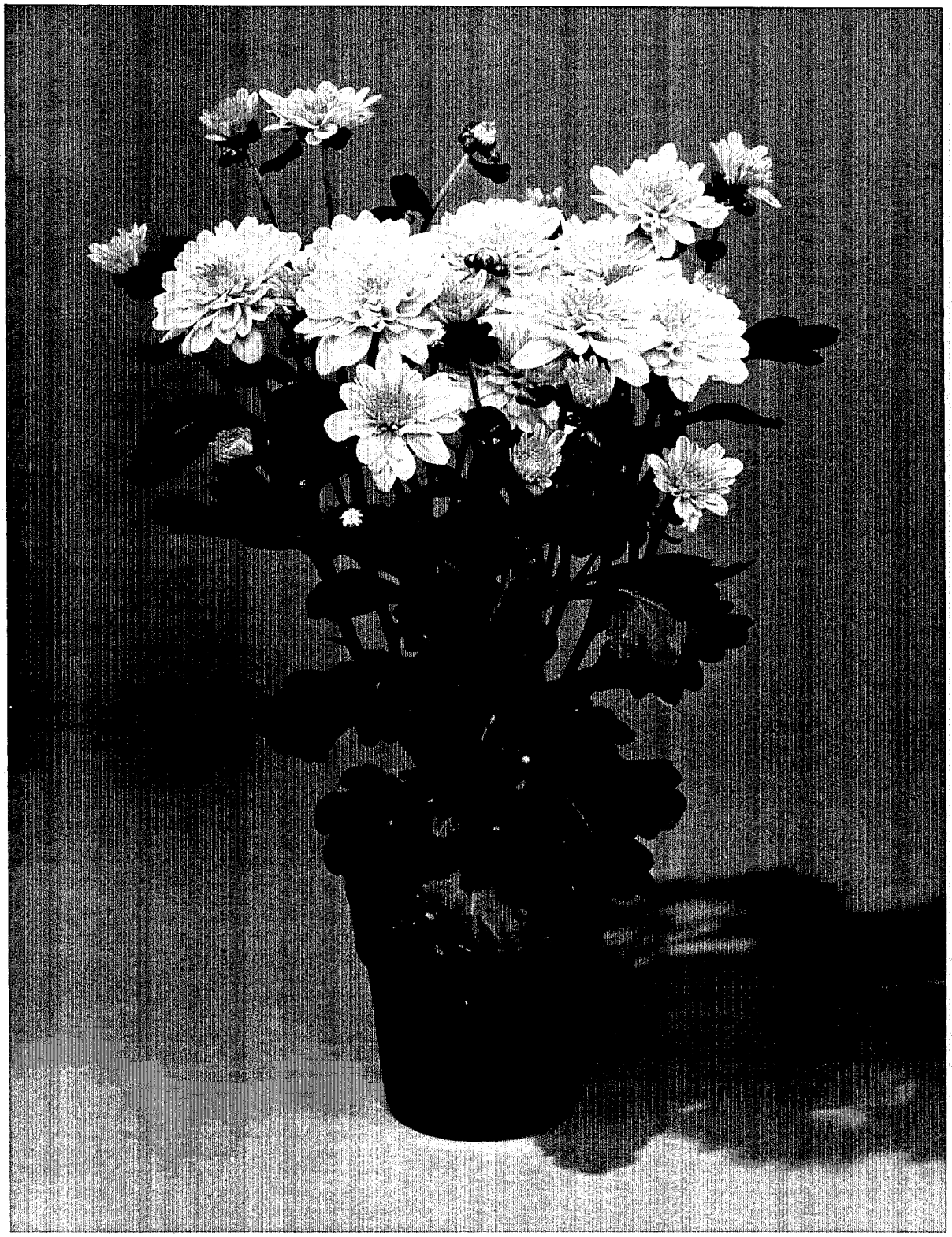

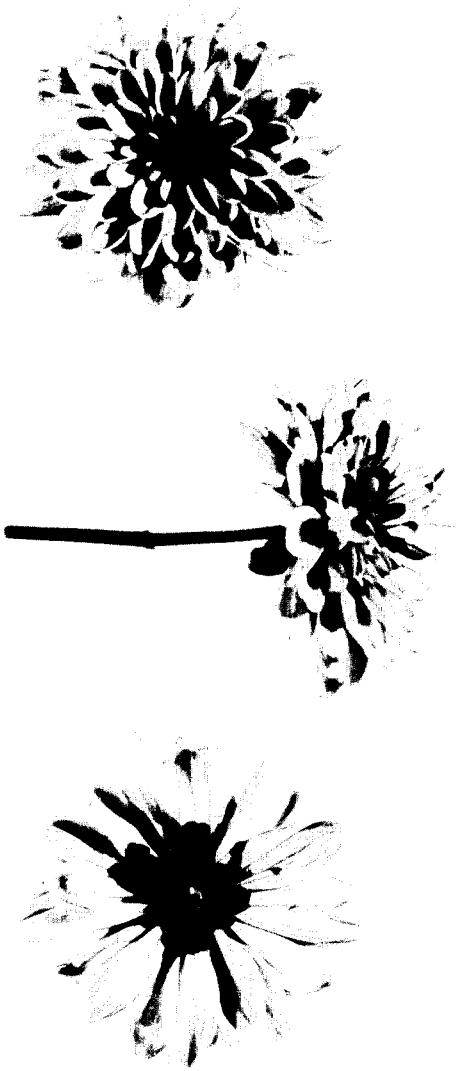

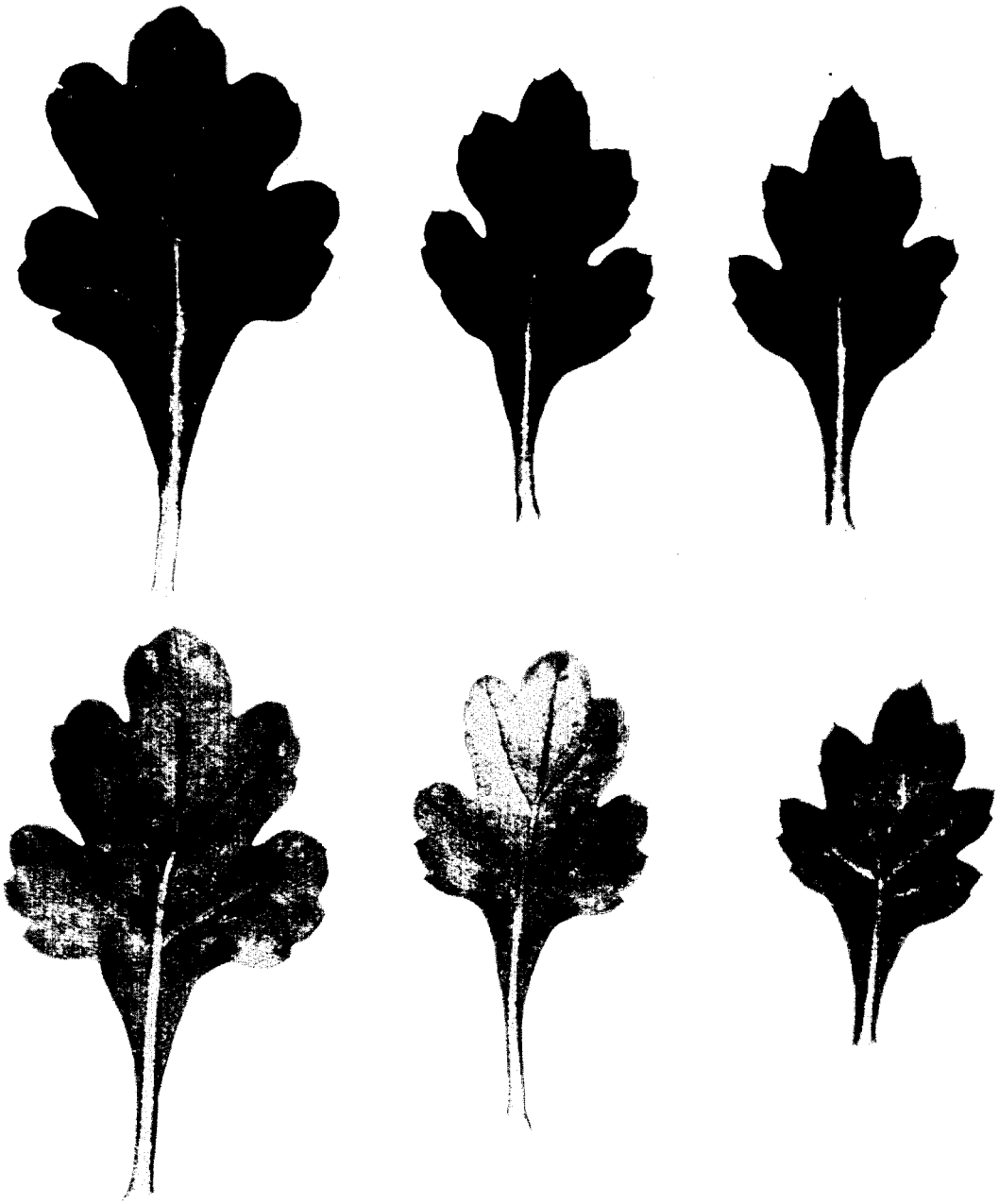

* * * * *